United States Patent
Bonelli et al.

(10) Patent No.: US 7,252,656 B2
(45) Date of Patent: Aug. 7, 2007

(54) DISPOSABLE ABSORBENT ARTICLES WITH WINGS HAVING CORRUGATED REGIONS AND METHODS OF MANUFACTURING THEREOF

(75) Inventors: Guido Bonelli, Pescara (IT); Nicola D'Alesio, Canosa Sannita (IT)

(73) Assignee: The Procter & Gamble Company, Cincinnati, OH (US)

( * ) Notice: Subject to any disclaimer, the term of this patent is extended or adjusted under 35 U.S.C. 154(b) by 96 days.

(21) Appl. No.: 10/780,961

(22) Filed: Feb. 18, 2004

(65) Prior Publication Data

US 2005/0182378 A1  Aug. 18, 2005

(51) Int. Cl.
*A61F 13/20* (2006.01)
(52) U.S. Cl. .................... 604/385.04; 604/385.01; 604/385.05
(58) Field of Classification Search ........... 604/385.04, 604/385.05
See application file for complete search history.

(56) References Cited

U.S. PATENT DOCUMENTS

| | | | |
|---|---|---|---|
| 4,223,063 A | 9/1980 | Sabee | |
| 4,834,741 A | 5/1989 | Sabee | |
| 4,940,462 A * | 7/1990 | Salerno | ........... 604/387 |
| 5,156,793 A | 10/1992 | Buell | |
| 5,221,276 A | 6/1993 | Battrell | |
| 5,354,400 A | 10/1994 | Lavash | |
| 5,518,801 A * | 5/1996 | Chappell et al. | ........... 428/152 |
| 5,558,663 A * | 9/1996 | Weinberger et al. | ........ 604/387 |
| 5,723,087 A | 3/1998 | Chappell | |
| 5,891,121 A * | 4/1999 | Redwine et al. | ........... 604/387 |
| 5,993,431 A * | 11/1999 | McFall et al. | ......... 604/385.24 |
| 6,059,764 A * | 5/2000 | Osborn, III et al. | .... 604/385.22 |
| 6,358,233 B1 * | 3/2002 | Taylor | ............ 604/385.04 |
| 6,383,169 B1 * | 5/2002 | Mills et al. | ........... 604/385.02 |
| 6,500,159 B1 * | 12/2002 | Carvalho | ............ 604/385.01 |
| 6,616,646 B2 | 9/2003 | Wada | |
| 2003/0224146 A1 | 12/2003 | Raidel | |

FOREIGN PATENT DOCUMENTS

| | | |
|---|---|---|
| EP | 0 695 542 A1 | 2/1996 |
| EP | 0 755 235 B1 | 3/1999 |
| EP | 0 726 751 B1 | 3/2000 |
| EP | 1 070 493 A2 | 1/2001 |
| EP | 0 606 358 B1 | 5/2001 |
| WO | WO 95/28137 | 10/1995 |

(Continued)

OTHER PUBLICATIONS

PCT International Search Report dated Jan. 8, 2005.

*Primary Examiner*—Tatyana Zalukaeva
*Assistant Examiner*—Ginger T. Chapman
(74) *Attorney, Agent, or Firm*—Roddy M. Bullock; David M. Weirich; Ken K. Patel

(57) ABSTRACT

A disposable absorbent article with one or more side flaps or wings, having at least one corrugated region, is disclosed. The corrugated region includes a corrugated material having a multiplicity of ridges and recesses, a release material opposed to the corrugated material, and a multiplicity of glue strips between the corrugated material and the release material. The glue strips are attached to the crests of the ridges of the corrugated material. Also, methods of fabricating a composite material including the corrugated region are also disclosed.

20 Claims, 12 Drawing Sheets

FOREIGN PATENT DOCUMENTS

| | | |
|---|---|---|
| WO | WO 97/12576 A1 | 4/1997 |
| WO | WO 97/12577 A1 | 4/1997 |
| WO | WO 97/15261 A1 | 5/1997 |
| WO | WO 97/21411 A1 | 6/1997 |
| WO | WO 97/33545 A1 | 9/1997 |
| WO | WO 97/39711 A1 | 10/1997 |
| WO | WO 97/39712 A1 | 10/1997 |
| WO | WO 98/05285 | 2/1998 |

* cited by examiner

DISPOSABLE ABSORBENT ARTICLES WITH WINGS HAVING CORRUGATED REGIONS AND METHODS OF MANUFACTURING THEREOF

FIELD OF THE INVENTION

The present invention relates to disposable absorbent articles with wings or side flaps, having corrugated regions and to methods of manufacturing thereof.

BACKGROUND OF THE INVENTION

Disposable absorbent articles with wings refer herein to personal care articles for absorbing bodily discharges. Typically, the articles having wings include catamenial napkins for absorbing menses (as well as other vaginal exudates), panty liners, adult incontinence pads for absorbing urine, and the like. These wings have been used to provide certain functions including integrating the article with the panties of a wearer for proper positioning of the article on the body of the wearer and preventing panties from "staining" by excretions when the article fails to prevent leakage. However, the panties containing an article with its wings wrapped around the crotch area of the panties can cause certain bodily discomfort to the wearer, caused by changes in the width and shape in the crotch area of the panties, often affected by the wrapped wings. Another cause of the bodily discomfort can result from the panties loosing elastic capability to stretch and contrast in response to bodily movements of the wearer.

FIG. 1 shows a photograph of a conventional wing 2 of a disposable absorbent article, wrapped or folded around a panty edge 3 of the panties 6 in the crotch area 7. It can be seen that the folded edge 5 of the conventional wing 2 does not follow the curvature 8 of the panty edge 3, thus, creating a distance 9 between the edge 3 and the folded edge 5, changing the width and the shape of the crotch area of the panties containing a feminine article with folded wings. It can be also seen that there are wrinkles 4 in the folded conventional wing 2, also capable of contributing to the bodily discomfort of a wearer.

Furthermore, the folded edge 5 of the conventional wing 2 of FIG. 1, typically tends to resist to stretching or contraction when the panty edge 3, often having elastic properties, stretches or contracts during wear of the panties 6 by a wearer. This deficiency of the conventional wing 2 to accommodate the elastic capability of the panty edge 3, can also contribute to bodily discomfort of a wearer.

Therefore, it would be beneficial to provide a disposable absorbent article with wings, which, during folding by a wearer around the edges of the panties, are capable of conforming to the curvature of the edges to improve bodily comfort of the wearer. Furthermore, it would be beneficial to provide a feminine hygiene article with wings, which, during wear by a wearer, are capable to stretch or contract to accommodate stretching or contracting of the elastic edges of the panties. And finally, it would be beneficial to provide a method for manufacturing a material for the wings capable of providing the above benefits.

SUMMARY OF THE INVENTION

In one aspect, the present invention is directed to a disposable absorbent article having one or more wings. The article includes a fluid-pervious topsheet, a fluid-impervious backsheet opposing said topsheet, and an absorbent core disposed between said topsheet and said backsheet, said article has a longitudinal direction and a transverse direction perpendicular thereof. Said one or more wings extend in said transverse direction and include at least one corrugated region including a multiplicity of ridges and recesses alternating with each other, said ridges rising toward a garment-facing surface of said article and having glue strips attached to crests of said ridges. The article further includes a release material for covering said at least one corrugated region, said release material contacting said glue strips. The disposable absorbent article is a feminine hygiene article for absorbing menses or a light incontinence article for absorbing urine.

In another aspect, the backsheet of the disposable absorbent article of the present invention can include at least one corrugated region.

In another aspect, the present invention is directed to a method of producing a composite material for use as a wing and/or a backsheet of the disposable absorbent article of the present invention. The composite material of the present invention can include a corrugated material, a release material opposed thereto, and a multiplicity of glue strips disposed between the release material and the corrugated material and attached to the crests of the corrugated material. The method includes the step of providing at least two corrugated rolls capable of counter-rotating and engaging with each other. Said ring-rolls can have a multiplicity of ridges and recesses disposed perpendicularly to axes of rotation of said corrugated rolls, said ridges being separated from each other at a pitch. The method further includes the step of providing a first material between said corrugated rolls for deforming said first material into a corrugated material having a multiplicity of ridges and recesses. The method further includes the step of heat-treating said corrugated material at a temperature less than the melting temperature of said first material. The method further includes the step of providing a release material having a multiplicity of glue strips disposed in a machine direction at said pitch therebetween. The method further includes the step of combining said release material with said corrugated material, wherein said multiplicity of glue strips are attached to crests of said ridges of said corrugated material to form said composite material.

Alternatively, the method of the present invention can include a glue-covered roll for transferring the glue from said glue-covered roll to said crests of said ridges of said corrugated material.

All documents cited are, in relevant part, incorporated herein by reference; the citation of any document is not to be construed as an admission that it is prior art with respect to the present invention.

BRIEF DESCRIPTION OF THE DRAWINGS

In the drawings, like reference numbers indicate identical or functionally similar elements.

DETAILED DESCRIPTION OF THE INVENTION

Definitions

Figure 1:
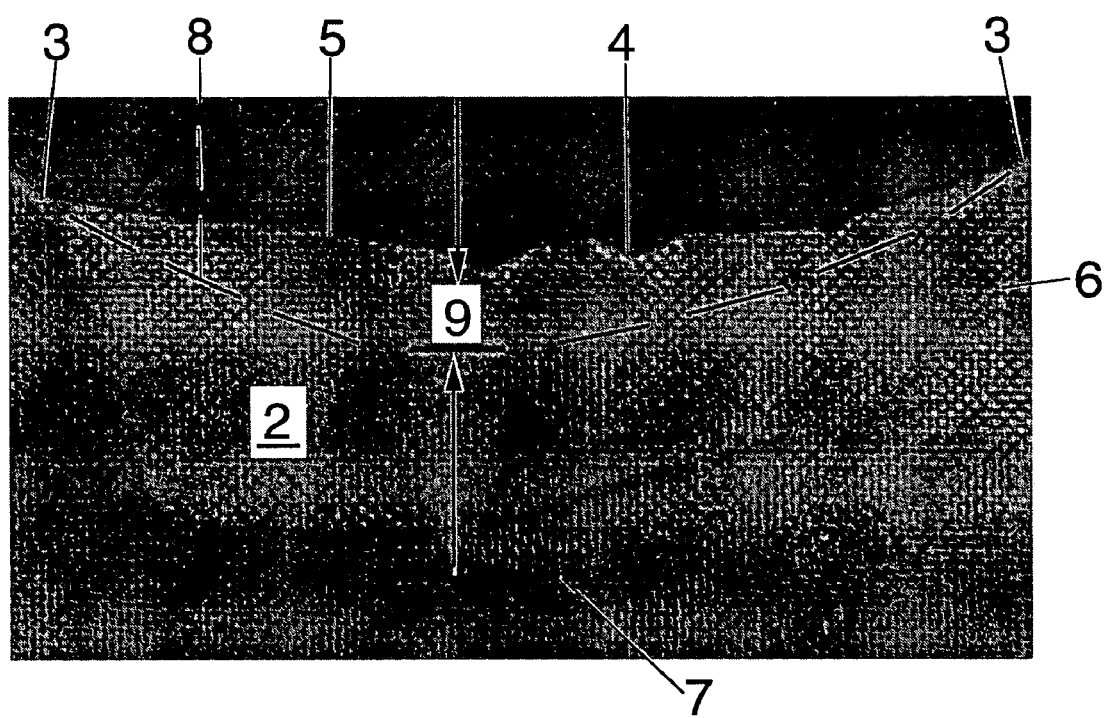
FIG. 1 is a photograph illustrating a conventional wing of a disposable absorbent article, wrapped or folded around a curved edge of the panties in the crotch area, wherein the conventional folded wing does not conform to the curvature of the panty edge.

Within the scope of this specification, each term or phrase below will include the following meaning or meanings. These terms, however, may be defined further with additional language in other portions of the specification.

The term "disposable absorbent article" refers herein to a device that normally absorbs and retains bodily fluids. The term includes devices that are placed against or in proximity to the body of a wearer to absorb and contain the excreta and/or exudates discharged from the body, and can include such personal care articles as catamenial napkins, panty liners, adult incontinence pads, baby diapers, wound dressings, and the like. Specifically, the present invention is concerned with disposable absorbent articles having side flaps or wings. Typically, the articles having wings can include catamenial napkins for absorbing menses (as well as other vaginal exudates) and adult incontinence pads for absorbing urine. However, it should be noted, that the present invention can include any disposable absorbent article having side wings or flaps.

The term "disposable" is used herein to describe products that generally are not intended to be laundered or otherwise restored, or extensively reused in their original function.

The term "body-facing surface" refers herein to a surface oriented toward the body when fitted to a wearer.

The term "garment-facing surface" refers herein to a surface oriented toward the garment, i.e. opposite to the body-facing surface, when fitted to a wearer.

The term "fan" refers herein to a configuration of a corrugated area of a folded wing of disposable feminine hygiene article, wherein the distance between adjacent corrugations at the panty edge is smaller than the distance between the adjacent corrugations disposed farther from the panty edge.

The term "longitudinal" refers herein to a line, axis, or direction in the plane of the disposable absorbent article that is generally aligned with (e.g., approximately parallel to) a vertical plane which bisects a standing wearer into left and right body halves when the article is worn.

The terms "transverse" or "lateral" are interchangeable herein and refer to a line, axis, or direction that is perpendicular to the longitudinal direction.

The term "web" refers herein to any continuous material, including a film, a non-woven fabric, or any combination thereof, having a single layer or multiple layers.

The term "non-woven" refers herein to a material made from continuous filaments and/or discontinuous fibers, without weaving or knitting by processes such as spun-bonding and melt-blowing. The non-woven material can comprise one or more layers of non-woven material, wherein each layer can include continuous filaments or discontinuous fibers.

The term "film" refers herein to any polymeric film made by a process that includes extrusion of a polymeric material through a narrow slot of a die. The polymeric film can be impervious to a fluid and pervious to an air vapor.

The terms "machine direction" or "web direction" are interchangeable herein and refer to a direction of travel of web(s) in production of disposable absorbent articles.

The term "cross-machine direction" refers to a direction that is generally perpendicular to the machine direction.

Description

FIG. 1 is a photograph illustrating a conventional wing 2 of a disposable absorbent article, wrapped or folded around a curved edge 3 of the panties 6 in the crotch area 7, wherein the folded edge 5 of the conventional wing 2 does not conform to the curvature 8 of the panty edge 3, thus, creating a distance 9 between the folded edge 5 and the curvature 8 of the panty edge 3. This failure to fold around the curvature 8 can also result in wrinkles 4. As described above, such conditions can contribute to bodily discomfort of a wearer. In addition, as noted above, the folded edge 5 of the conventional wing 2 of FIG. 1, typically tends to resist stretching or contraction when the panty edge 3, often having elastic properties, is capable of stretching or contraction during wear of the panties 6 by a wearer. This deficiency of the conventional wing 2 can also contribute to the bodily discomfort of the wearer.

Figure 2:
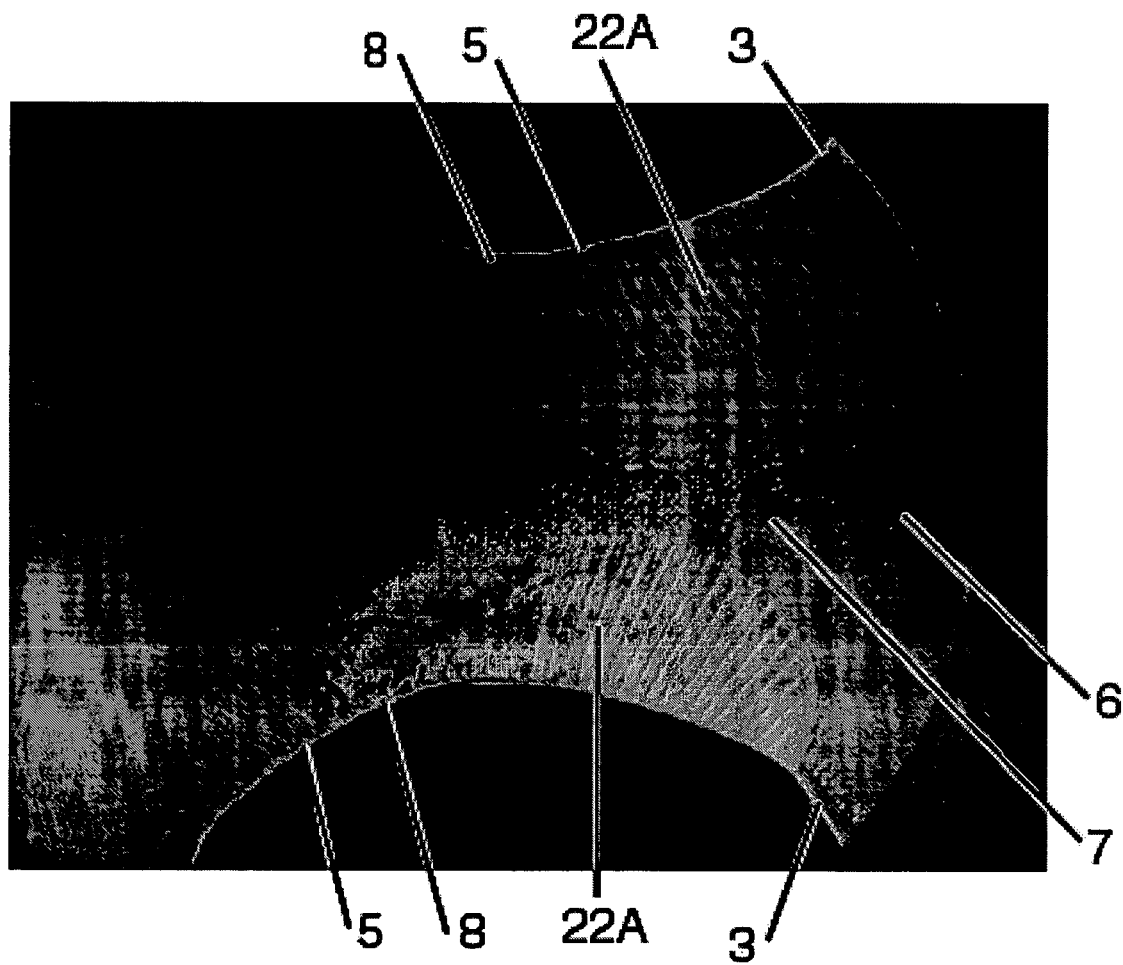
FIG. 2 is a photograph illustrating one exemplary embodiment of the wings of the disposable absorbent articles of the present invention, wrapped or folded around the curved edges of the panties in the crotch area, wherein the folded wings conform to the curvatures of the panties edge.
Figure 3:
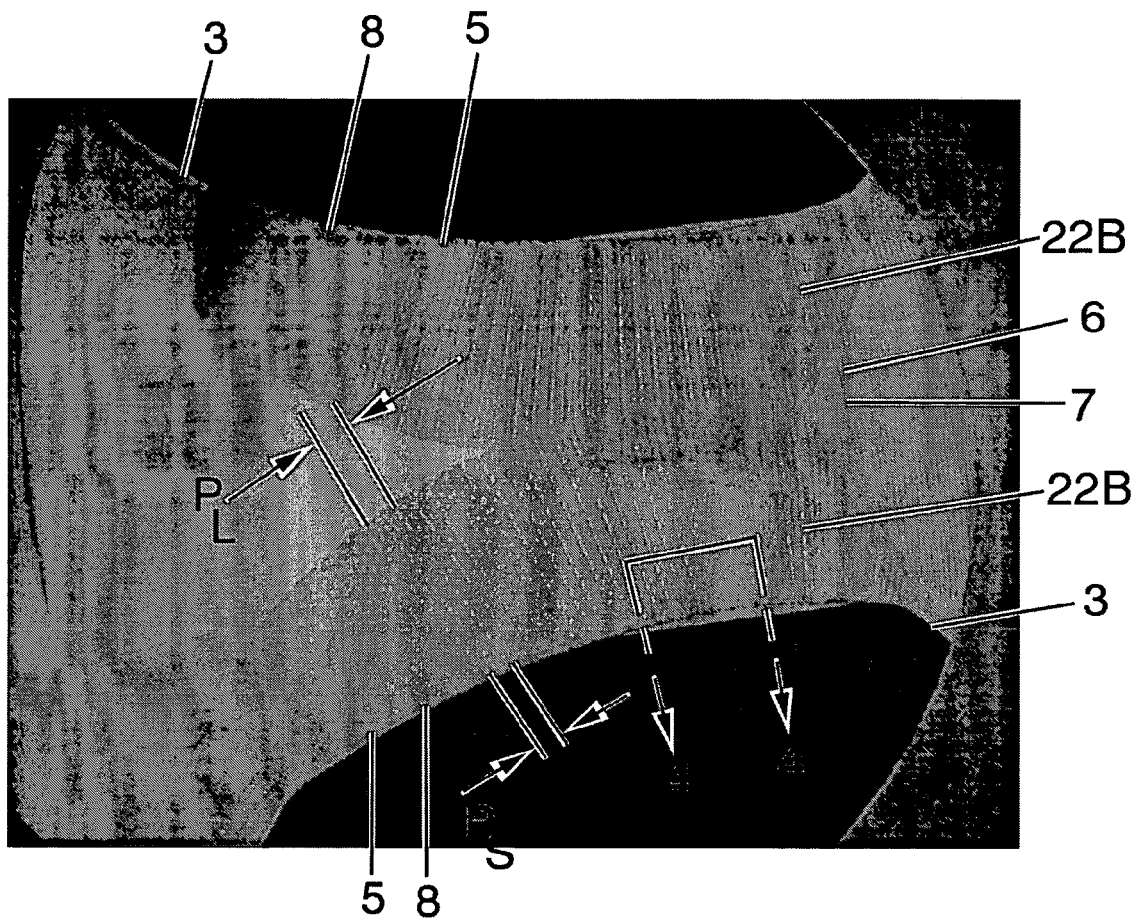
FIG. 3 is a photograph illustrating another exemplary embodiment of the wings of the present invention, wrapped or folded around the curved edges of the panties in the crotch area, wherein the folded wings conform to the curvatures of the panties edge.

FIGS. 2 and 3 show photographs illustrating two exemplary embodiments of the wings 22A and 22B, respectively, of the disposable absorbent article of the present invention, wrapped or folded around the panty edges 3 of the panties 6 in the crotch area 7, wherein the folded edges 5 of the wings 22A and 22B conform to the curvatures 8 of the panty edge 3, eliminating the undesired conditions shown in FIG. 1. In addition, as will be described below, the folded edges 5 of the wings of the present invention can stretch or contract together with the panty edge 3, thus reducing the resistance to stretching or contraction typical of the conventional wings, noted above. Therefore, the above capabilities of the wings of the absorbent articles of the present invention can eliminate the undesired conditions described above with respect to conventional wings, thus, contributing to the bodily comfort of a wearer.

Figure 4:
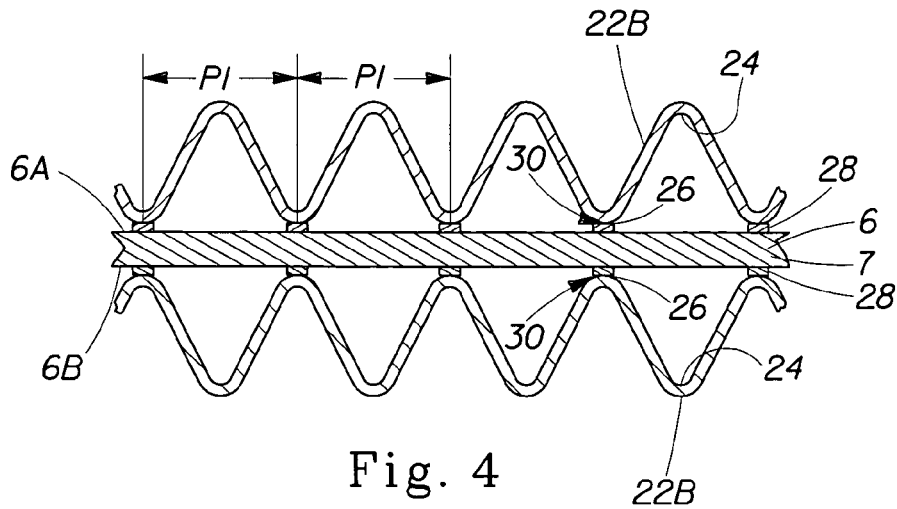
FIG. 4 is a cross-sectional view of the wing of the present invention, wrapped or folded around the panty edge and affixed by glue to both opposing surfaces of the panties at the crests of the ridges of the corrugations, taken along line 4-4 of FIG. 3.

FIG. 4 is a cross-sectional view of the exemplary wings 22B of the present invention, wrapped or folded around the panty edge 3, taken along line 4-4 of FIG. 3. (It should be noted, however, that the same cross-sectional view can be shown for wings 22A of FIG. 2).

Figure 5:
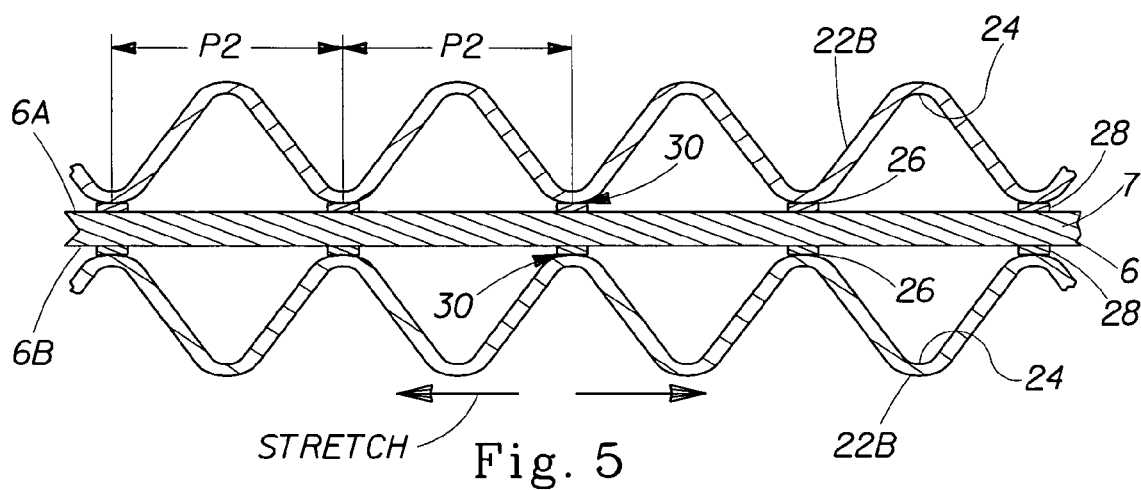
FIG. 5 is a cross-sectional view showing the corrugations and the panties edge of FIG. 4 in a stretched state.
Figure 6:
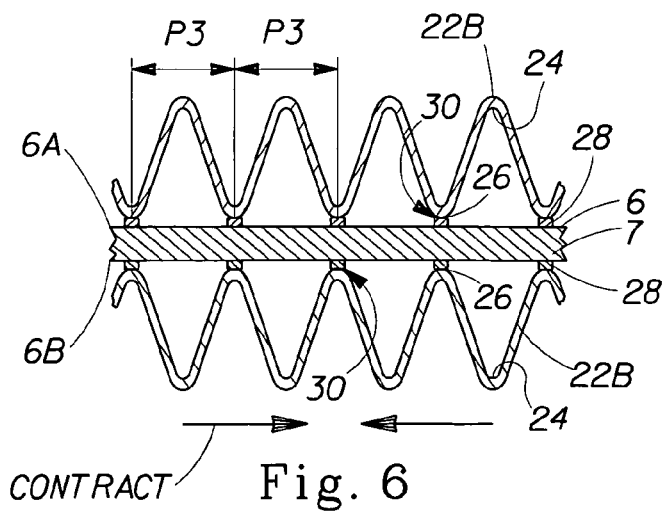
FIG. 6 is a cross-sectional view showing the corrugations and the panties edge of FIG. 4 in a contracted state.

The wings of the present invention, as shown in FIG. 4, have corrugated shape comprising a multiplicity of alternating groves 24 and ridges 26. When folded around the panty, the ridges 26 are affixed to both opposing surfaces 6A and 6B of the panties 6 in the crotch area 7 including the panty edge 3, with glue 28 disposed between the crests 30 of the ridges 26 and each of the respective surfaces 6A and 6B. Thus, the wings 22B are anchored to the panties 6 only at the crests 30 of the ridges 26, i.e., a multiplicity of ridges 26 separated from each other at a suitable interval, for example, a pitch P1. (It should be noted that the term "crest" of the ridge 26 refers herein not to a point but to a relatively small area at the top of the ridge 26, which could in practice suitably vary in size. Such construction enables the expansion or contraction between the corrugations, i.e., between the ridges 26, during stretching or contraction of the panties 6 including the panty edge 3, as shown in FIGS. 5 and 6. FIG. 5 shows the corrugations of the wings 22B being stretched, in comparison with those in FIG. 4, resulting in a pitch P2 between the ridges 26 being greater than the pitch P1 of FIG. 4. FIG. 6 shows the corrugations of the wings 22B being contracted, in comparison with FIG. 4, resulting in a pitch P3 between the ridges 26 being smaller than the pitch P1 of FIG. 4.

Figure 7:
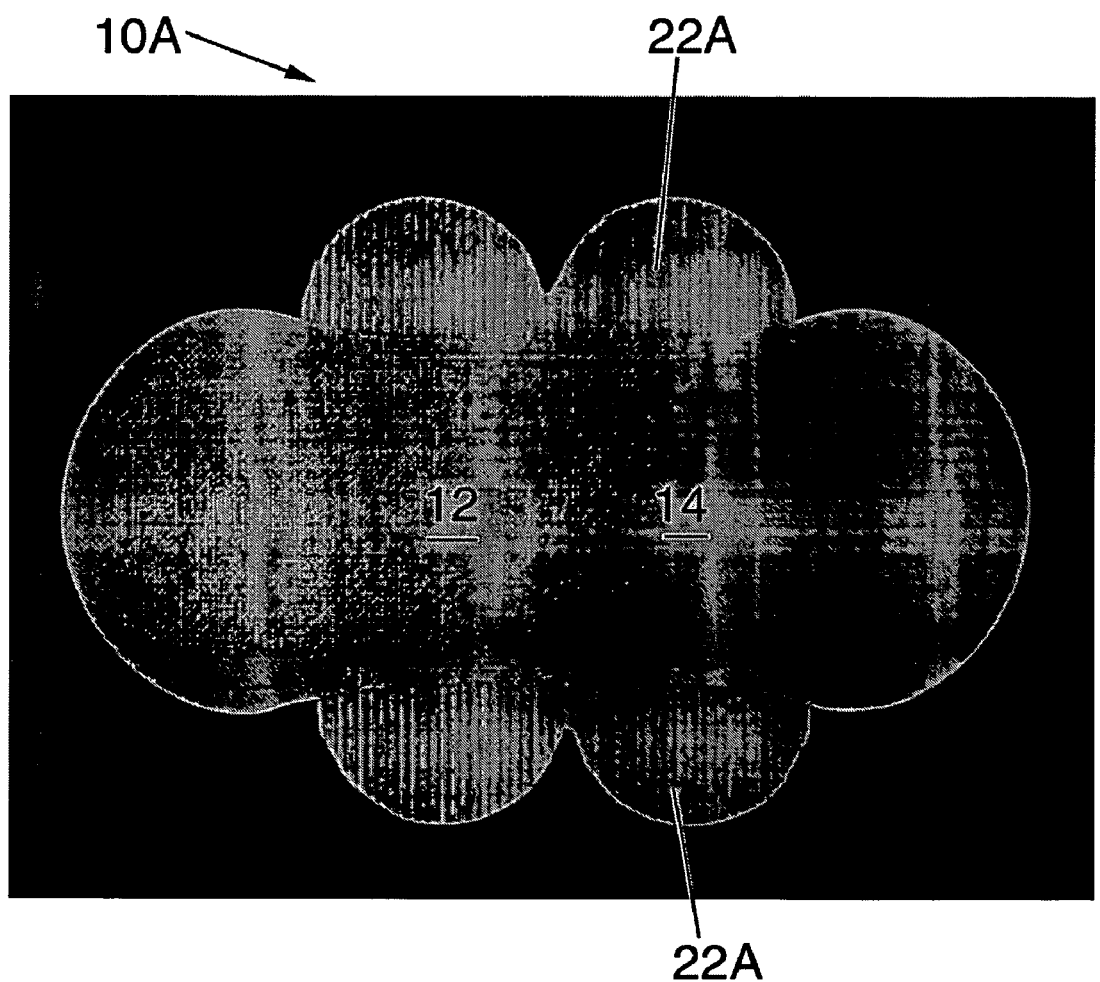
FIG. 7 is a photograph illustrating a plan view one exemplary embodiment of a disposable absorbent article of the present invention, in particular, a feminine hygiene article oriented with its body-facing surface toward the viewer.

FIG. 7 is a photograph illustrating a plan view of one exemplary embodiment of a disposable absorbent article of the present invention, in particular, a feminine hygiene article 10A, oriented with its body-facing surface 14 toward the viewer, i.e., a topsheet 12 (for passing excreted fluid, such as menstrual blood and/or urine, from a wearer through the topsheet 12) facing the viewer. The article 10A includes wings 22A before they are wrapped or folded around the crotch area as shown in FIG. 2.

Figure 8:
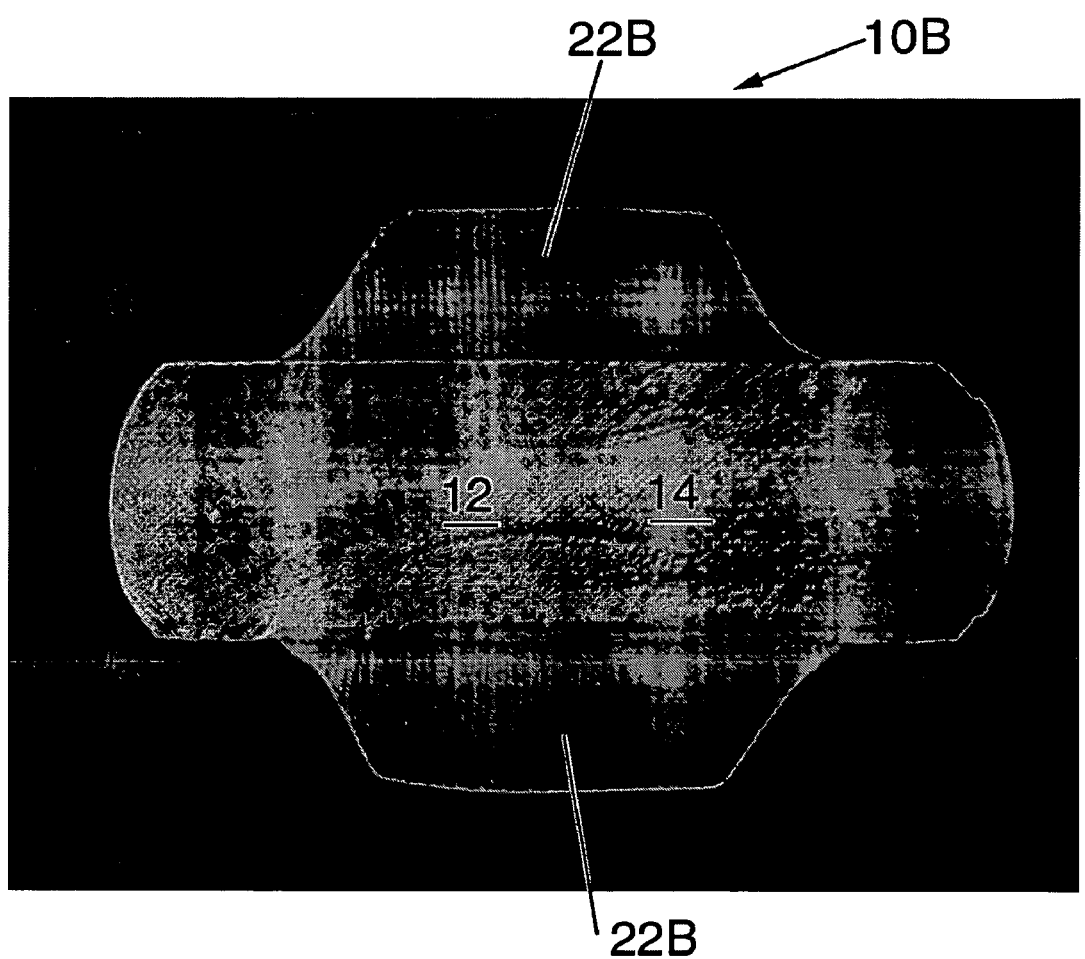
FIG. 8 is a photograph illustrating another exemplary embodiment of a disposable absorbent article of the present invention, in particular, a feminine hygiene article oriented with its body-facing surface toward the viewer.

FIG. 8 is a photograph illustrating another exemplary embodiment of a disposable absorbent article of the present invention, in particular, a feminine hygiene article 10B, oriented with its body-facing surface 14 toward the viewer, i.e., a topsheet 12 (for passing excreted fluid, such as menstrual blood and/or urine, from a wearer through the topsheet 12) facing the viewer. The article 10B includes wings 22B before they are wrapped or folded around the crotch area as shown in FIG. 2.

Figure 9:
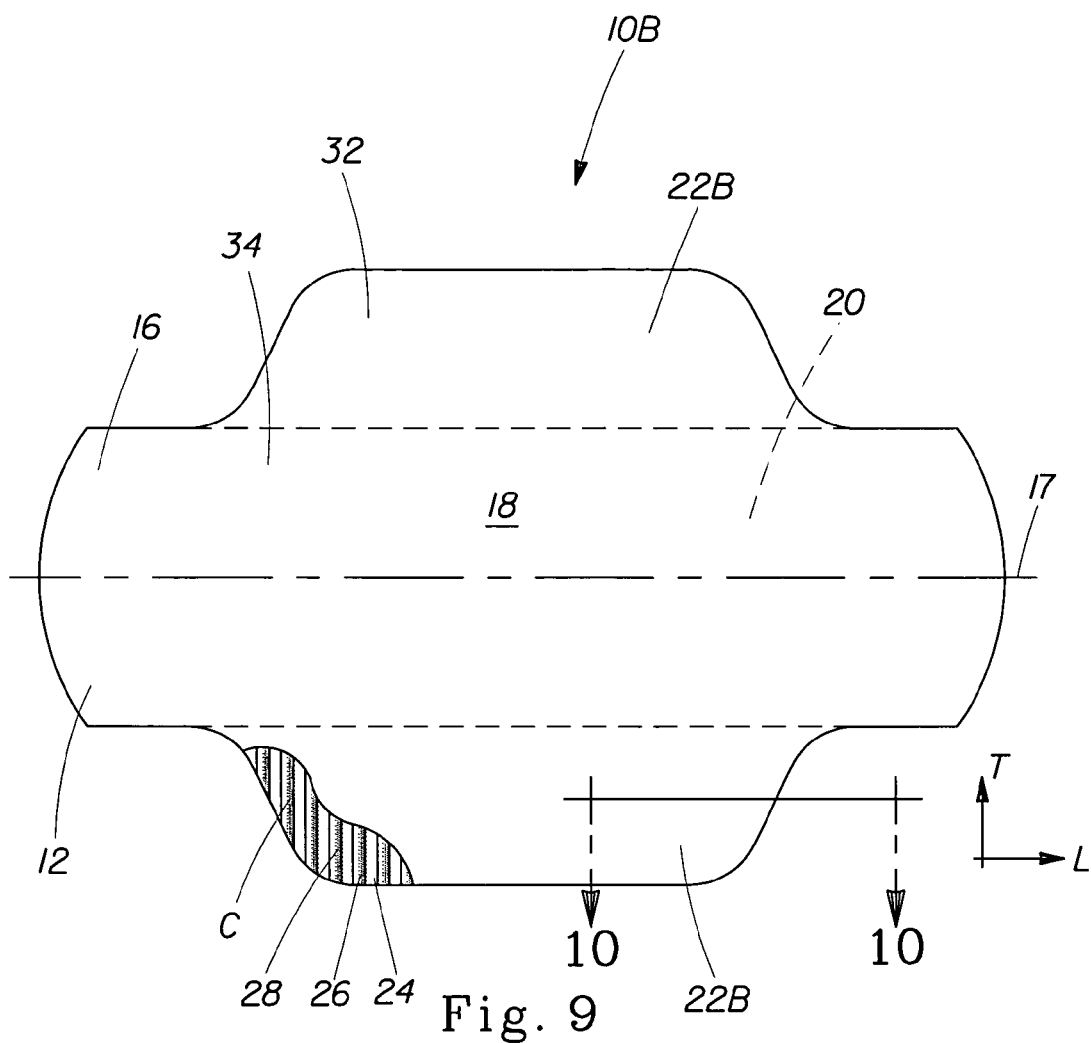
FIG. 9 is a plan view of the feminine hygiene article of FIG. 8, oriented with its garment-facing surface toward the viewer.

FIG. 9 is a plan view of the article 10B of FIG. 8, oriented with its garment-facing surface 18 toward the viewer, i.e., a fluid impervious backsheet 16 for preventing the excreted fluid from passing through the backsheet 16) facing the viewer. The article 10B includes an absorbent core 20 sandwiched between the topsheet 12 and the backsheet 16 for absorbing the excreted fluid passed through the topsheet 12. Typically, the article 10B has a longitudinal centerline 17, preferably symmetrically dividing the article 10B in a longitudinal direction L. As shown, the longitudinal direction L is directed parallel to the longitudinal centerline 17 and perpendicular to a transverse or lateral direction T.

The article 10B preferably includes two wings 22B extending laterally in opposing directions from the absorbent core 20. Each of the wings 22B includes at least one corrugated area C having glue strips 28 at the crests of the ridges, as described above. The corrugated area C can extend partially or throughout the wing 22B. (It should be noted, as will be described below, that the corrugated area C could also include a portion or a whole area of the backsheet 16.)

The article 10B further comprises a release material 32 for covering the glue 28. In addition, the article 10B can further include a release material 34 for covering the backsheet 16, which can be also covered with glue (not shown) for attaching the garment-facing surface 18 of the backsheet 16 to the panties of a wearer.

Figure 10:
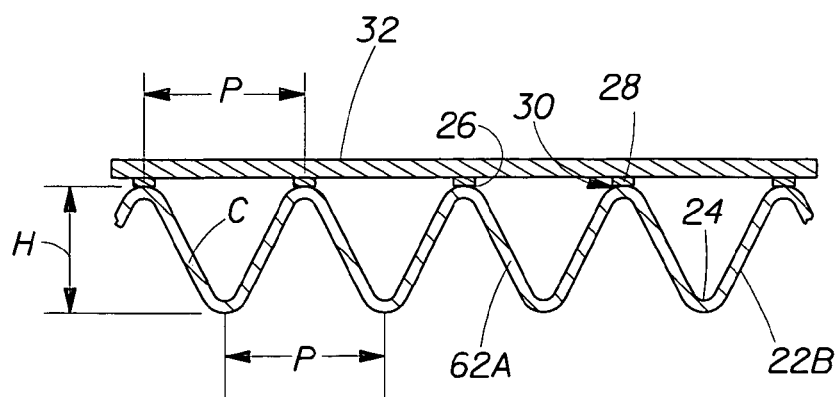
FIG. 10 is an enlarged cross-sectional view of a corrugated region of the feminine hygiene article of FIG. 9, taken along line 10-10.

FIG. 10 is an enlarged cross-sectional view of a corrugated region of the article of FIG. 9, taken along line 10-10, showing the corrugated region C of the wing 22B, comprising ridges 26 and recesses or groves 24, attached to the release material 32 with glue 28 at the crests 30 of the ridges 26.

Topsheet

The topsheet 12 of the feminine hygiene articles of the present invention is preferably compliant, soft feeling, and non-irritating to the wearer's skin. The topsheet 12 can be also elastically stretchable in one or two directions. As noted above, the topsheet 10 is inherently fluid-pervious, permitting fluids (e.g., menses and/or urine) to readily penetrate through its thickness. A suitable topsheet 12 can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Further, the topsheet 12 can be selected from high loft nonwoven topsheets and apertured formed film topsheets. Suitable formed films are described in U.S. Pat. Nos. 3,929,135; 4,324,246; 4,342,314; 4,463,045; and 5,006,394. Further, microapertured formed film topsheets are disclosed in U.S. Pat. Nos. 4,609,518 and 4,629,643.

Further, the topsheet 12 can have not a homogeneous distribution of fluid passageways, but only a portion of the topsheet 12 comprising fluid passageways is also contemplated by the present invention. Typically, such topsheets would have the fluid passageways oriented such that they result in a centrally permeable and peripherally impermeable topsheet for fluids.

Further, the body-facing surface of the formed film topsheet can be hydrophilic so as to help fluid to transfer through the topsheet 12 faster than if the body-facing surface was not hydrophilic. Alternatively, the body-facing surface of the topsheet can be made hydrophilic by treating it with a surfactant such as is described in the above referenced U.S. Pat. No. 4,950,254.

Backsheet

The backsheet 16 prevents the excretes absorbed and contained in the absorbent core 20 from wetting undergarments and other garment articles that can come in contact with the feminine hygiene article of the present invention. As noted above, the backsheet 16 is impervious to fluids (e.g., bodily excretes such as menses and/or urine) and is preferably manufactured from a thin plastic film, although other flexible fluid-impervious materials can also be used. The backsheet 16 needs to be compliant and will readily conform to the general shape and contours of the human body. The backsheet 16 preferably also can have characteristics allowing it to elastically stretch in one or two directions.

Further, the backsheet 16 can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm to about 0.051 mm. Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet 16 is preferably embossed and/or matte finished to provide a more cloth like appearance. Further, the backsheet 16 can permit vapors to escape from the absorbent structure (i.e., be breathable) while still preventing exudates from passing through the backsheet. In particular, for feminine hygiene articles having a low quantity of fluid to absorb according to their intended use, it is possible to utilize apertured hydrophobic polymeric films having directional fluid transport—such as those disclosed above for the topsheet 10—toward the absorbent core 20, as breathable backsheets.

Absorbent Core

The absorbent core 20 of the feminine hygiene article of the present invention can be any suitable absorbent core capable of absorbing excreted fluid such as menstrual blood and/or urine. For example, the absorbent core 20 can optionally comprise the following components (not shown): (a) a primary fluid distribution layer; (b) a secondary fluid distribution layer; (c) a fluid storage layer; (d) a fibrous ("dusting") layer underlying the storage layer; and (e) other optional components.

(a) Primary Fluid Distribution Layer

The primary distribution layer typically underlies the topsheet 12 and is in fluid communication therewith. The topsheet 12 transfers the acquired excreted fluid to this primary distribution layer for ultimate distribution to the storage layer. This transfer of fluid through the primary distribution layer occurs not only in the thickness, but also along the length and width directions of the absorbent article.

(b) Secondary Fluid Distribution Layer

The secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized.

(c) Fluid Storage Layer

The fluid storage layer can be positioned in fluid communication with, and typically underlying the primary or secondary distribution layers. The fluid storage layer can comprise absorbent gelling materials and/or other absorbent materials, which can form the carrier matrix for the absorbent gelling materials. Absorbent gelling materials are usually referred to as "hydrogels," "superabsorbent" "hydrocolloid" materials. Absorbent gelling materials are those materials that, upon contact with aqueous fluids, especially aqueous body fluids, imbibe such fluids and, thus, form hydrogels. These absorbent gelling materials are typically capable of absorbing large quantities of aqueous body fluids, and are further capable of retaining such absorbed fluids under moderate pressures. These absorbent gelling materials can be in the form of discrete particles.

Further, the fluid storage layer can comprise solely absorbent gelling materials, or these absorbent gelling materials can be dispersed homogeneously or non-homogeneously in a suitable carrier or it can comprise solely an absorbent carrier material. Suitable carriers include cellulose fibers, in the form of fluff, tissues or paper such as is conventionally utilized in absorbent cores. Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Synthetic fibers can have a denier ranging of from about 3 denier per filament to about 25 denier per filament, or from about 5 denier per filament to about 16 denier per filament. Also, the fiber surfaces can be hydrophilic or treated to be hydrophilic. The storage layer can also include filler materials, such as Perlite, diatomaceous earth, Vermiculite, etc., that lower rewet problems.

Further, if dispersed non-homogeneously in a carrier, the storage layer can be locally homogeneous, i.e. have a distribution gradient in one or several directions within the dimensions of the storage layer. Non-homogeneous distribution can also refer to laminates of carriers enclosing absorbent gelling materials partially or fully. If laminates are used, they can be formed with or without absorbent gelling particles. In particular, thermally bonded air laid fibrous sheets or laminates and/or thermally bonded wet laid sheets or laminates have been found useful, especially, in the context of panty liners when no absorbent gelling material is used.

Further, the storage layer can comprise from about 15 to 100% absorbent gelling materials and from 0 to about 85% carrier. Suitable absorbent gelling materials for use herein will most often comprise a substantially water-insoluble, slightly cross linked, partially neutralized, polymeric gelling material. This material forms a hydro gel upon contact with water. Such polymer materials can be prepared from polymerizable, unsaturated, acid-containing monomers. Suitable unsaturated acidic monomers include those listed in U.S. Pat. No. 4,654,039 and reissued as RE 32,649. The monomers include acrylic acid, methacrylic acid, and 2-acrylamido-2-methyl propane sulfonic acid. The polymeric component formed from the unsaturated, acid-containing monomers can be grafted onto other types of polymer moieties such as starch or cellulose. Polyacrylate grafted starch materials of this type can be also included. The polymeric absorbent gelling materials that can be prepared from conventional types of monomers include hydrolyzed acrylonitrile grafted starch, polyacrylate grafted starch, polyacrylates, maleic anhydride-based copolymers and combinations thereof. While these absorbent gelling materials are typically in particle form, it is also contemplated that the absorbent gelling material can be in the form of macrostructures such as fibers, sheets, or strips.

(d) Fibrous ("Dusting") Layer

An optional component for inclusion in the absorbent core 20 can be a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of laminates or of macrostructures such as fibers, sheets, or strips, this fibrous "dusting" layer need not be included.

(e) Other Optional Components

The absorbent core 20 can include other optional components normally present in absorbent webs. For example, a reinforcing scrim can be positioned within the respective layers, or between the respective layers, of the absorbent cores. Such reinforcing scrims should be of such configuration as to not form interfacial barriers to fluid transfer, especially, if positioned between the respective layers of the absorbent core 12.

Another component, which can be included in the absorbent core 20 and provided close to or as part of the primary or secondary fluid distribution layer, are odor control agents. These can be selected from active carbon or coated active carbon, suitable zeolite or clay materials. These components can be incorporated in any desired form, but often are included as discrete, non-fibrous particles.

Wings

At least one, but preferably two wings (22A or 22B, for example) of the present invention can extend laterally from the absorbent core 20. The wings of the present invention can be separate components fixedly joined to the backsheet 16, to the topsheet 12, or to the both. Alternatively, the wings of the present invention need not be separate components, but they can be part of the backsheet 16, the topsheet 12, or both, extending laterally from the absorbent core 20. Therefore, the materials suitable for the wings of the present invention can include the materials described above with respect to the backsheet 16 and the topsheet 12.

As noted above, the wings of the present invention comprise at least one corrugated region C (as shown, for example, FIGS. 9 and 10) including a multiplicity of recesses or groves 24 and ridges 26, alternating with each other, wherein the ridges 26 rise toward the garment-facing surface 18 of the article and have a glue 28 attached to the crests 30 of the ridges 26.

Figure 11:
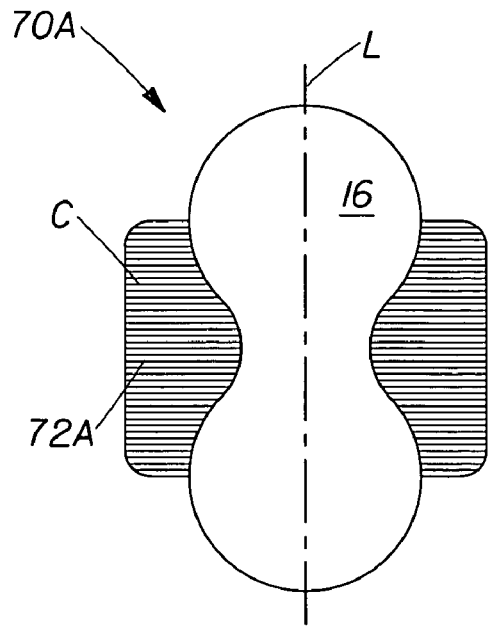
FIG. 11 is a simplified plan view of one embodiment of the disposable absorbent article of the present invention illustrating corrugations extending normally to a longitudinal centerline.
Figure 12:
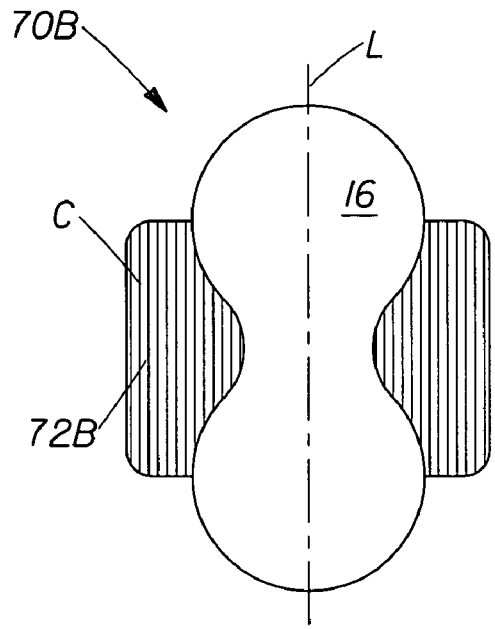
FIG. 12 is a simplified plan view of another embodiment of the disposable absorbent article of the present invention illustrating corrugations extending parallel to a longitudinal centerline.
Figure 13:
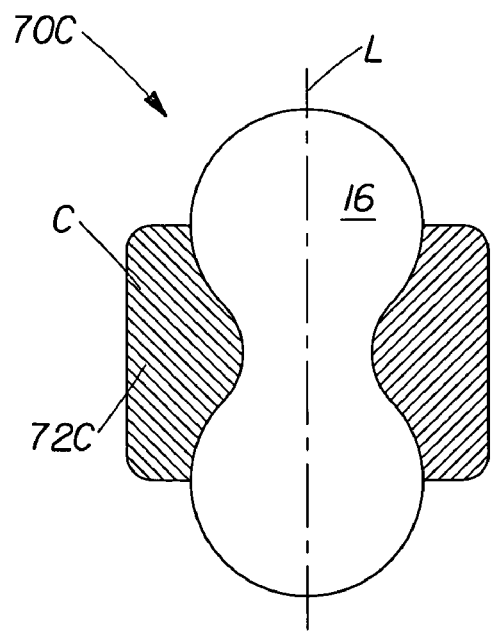
FIG. 13 is a simplified plan view of another embodiment of the disposable absorbent article of the present invention illustrating corrugations extending at an angle to a longitudinal centerline.
Figure 14:
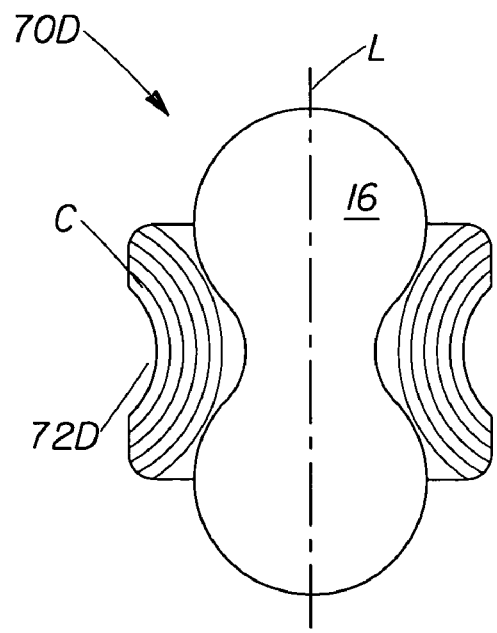
FIG. 14 is a simplified plan view of another embodiment of the disposable absorbent article of the present invention illustrating corrugations extending multi-directionally to a longitudinal centerline.
Figure 15:
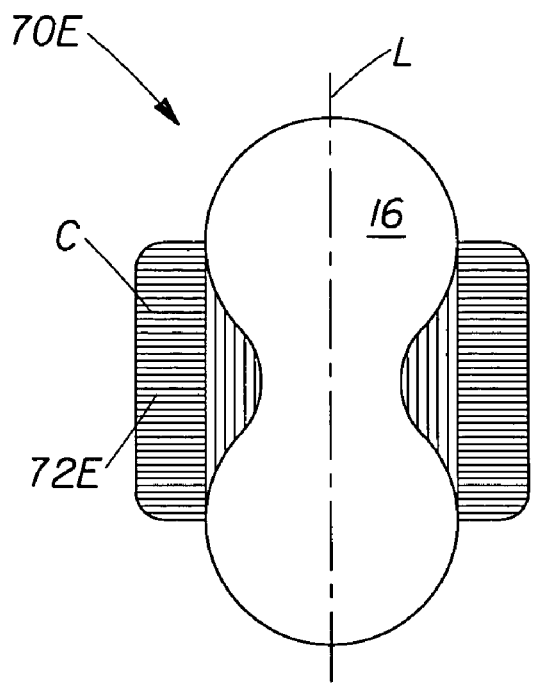
FIG. 15 is a simplified plan view of another embodiment of the disposable absorbent article of the present invention illustrating corrugations extending both normally and parallel to a longitudinal centerline.

As shown in FIGS. 7-9, the ridges 26 and the recesses 24 extend in the transverse direction T. However, the ridges 26 and the recesses 24 of the present invention can extend in various directions, as shown, for example, in FIGS. 11-15, which are simplified plan views of several exemplified embodiments of the articles of the present invention. FIG. 11 is a simplified plan view of a feminine hygiene article 70A of the present invention illustrating corrugations C in wings 72A, extending normally to a longitudinal centerline L. FIG. 12 is a simplified plan view of a feminine hygiene article 70B of the present invention illustrating corrugations in wings 72B, extending parallel to a longitudinal centerline L. FIG. 13 is a simplified plan view of a feminine hygiene article 70C of the present invention illustrating corrugations C in wings 72C, extending at an angle to a longitudinal centerline L. FIG. 14 is a simplified plan view of a feminine hygiene article 70D of the present invention illustrating corrugations C in wings 72D, extending multi-directionally to a longitudinal centerline L. FIG. 15 is a simplified plan view of a feminine hygiene article 70E of the present invention illustrating corrugations in wings 72E, extending both normally and parallel to a longitudinal centerline L.

Figure 16:
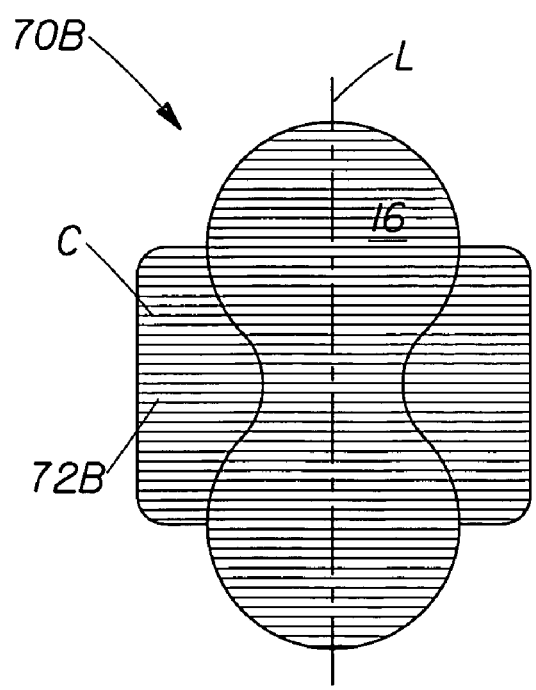
FIG. 16 is a simplified plan view of another embodiment of the disposable absorbent article of the present invention illustrating corrugations both in the wings and in the backsheet.

However, the corrugations of the present invention can be not only in the wings, but also in the backsheet of the feminine hygiene articles of the present invention. For example, as shown in FIG. 16, which is a simplified plan view of the feminine hygiene article 80 of the present invention having corrugations both in the wings 82 and in the backsheet 16. FIG. 16 shows, as an example, corrugations C extending normally to the longitudinal centerline L; however, as noted above with respect to the wings of the present invention, the corrugations C in the wings and the backsheet of the present invention can extend in any direction with respect to the longitudinal centerline L, as shown in FIGS. 11-15.

With respect to the wrinkles that can be often formed by conventional wings when they are wrapped or folded around the crotch of the panties, as illustrated, for example, in FIG. 1 (wrinkles 4), the wings of the present invention can be wrapped or folded by a user around the crotch area of the panties, without forming the undesired wrinkles. This elimination of wrinkles is due to a "fan" capability of the corrugated area of the wings of the present invention, best illustrated, for example, in FIG. 3. The term "fan" refers herein to a configuration of the corrugated area of a wrapped or folded wing, wherein the distance between adjacent corrugations (for example, ridges 26) at the panty edge 3 is smaller than the distance between the adjacent corrugations (for example, ridges 26) disposed farther from the panty edge 3. As illustrated in FIG. 3, the distance or pitch $P_S$ between the adjacent corrugations at the panty edge 3 is smaller than the distance or pitch $P_L$ between the adjacent corrugations disposed farther from the panty edge 3. This ability of the corrugations to "fan" results in elimination of the undesired wrinkles.

With respect to glue 28, it can comprise any suitable panty fastening glue typically used in the art of attaching disposable feminine hygiene articles to the panties, with pressure-sensitive glues being preferred. Examples of suitable glues include Century A-305-IV manufactured by the Century Glues Corporation, Instant Lock 34-2823 manufactured by the National Starch Company, 3 Sigma 3153 manufactured by 3 Sigma, and Fuller H-2238ZP manufactured by the H. B. Fuller Co. Other suitable glues are also described in U.S. Pat. No. 4,917,697 and International Patent Publications WO 92/04000, WO 93/01783, and WO 93/01785.

Prior to use of the feminine hygiene article 10, the panty fastening glue 28 is typically protected from contamination and from sticking to any surface where this is not desired, by a protective cover means 32 (FIGS. 9 and 10) such as a release material 32, typically including a silicone coated release paper, a plastic film or any other easily removable material. The protective material 32 can be provided as a single piece or in multiple pieces, e.g., to cover individual glue areas.

Referring to FIG. 10, the distance or pitch P between the adjacent ridges 26 (as well as the adjacent recesses 24) of the corrugated region C, can be any suitable pitch P within a range from about 1 mm to about 5 mm. Similarly, the height H of the ridges 26 (as well as the recesses 24) can be any suitable height H within a suitable range, for example, from about 1 mm to about 6 mm.

The corrugated region C of the present invention, including groves 24 and recesses 26 can be provided by deforming a web material (which can be flat) between two or more corrugated rolls, also known to one skilled in the art as ring rolls, engaged with each other at a certain depth. (This will be described in more detail below with respect to FIGS. 17 and 18.) The corrugated or ring-rolls have a multiplicity of ridges and recesses or groves, wherein the ridges of one of the rolls are engaged with the recesses or groves of the corresponding roll (FIG. 18). As a result of the corrugation or ring-rolling step, the flat web material becomes deformed into a corrugated material 62A (FIG. 10) having the pitch P between the adjacent ridges 26 (as well as between adjacent groves 24). The pitch P will generally correspond with the pitch between adjacent ridges of the engaged ring rolls. The height H of the bridges 26 (as well as the recesses 24) of the corrugated material 62A will generally depend on the depth of engagement of the ring rolls. The ring-rolling method is described in more detail in the following commonly assigned patents: U.S. Pat. No. 5,156,793 to Buell et al. and U.S. Pat. No. 5,723,087 to Chappell et al., all of which are hereby incorporated by reference herein. As shown, in particular, in U.S. Pat. No. 5,723,087 to Chappell et al., the ridges and recesses of the ring rolls can extend in any suitable direction in relation to the longitudinal or machine direction of the disclosed ring-rolling method.

However, in the present invention, in addition to the ring-rolling process described in the references above, the corrugation area C is also subjected to a heat treatment step during the ring-rolling step to provide memory to the deformed corrugated material (62A of FIG. 10) and, thus, greater stability of the dimensions of the deformed pith P and height H of the ridges 26 and recesses 24 of the corrugated area C. This will be also described in more detail below with respect to the method of the present invention of producing the corrugated material of the present invention, suitable for the wings of the present invention and, optionally, for the backsheet of the disposable absorbrent articles of the present invention.

With respect to the shape of the wings of the present invention, it should be noted that the corrugated wings of the present invention can have any suitable shape or configuration. For example, FIGS. 2 and 5 show wings 22A shaped as a "camel top" or a "heart top," and FIGS. 3 and 8 show wings 22B having a generally rectangular shape.

Method

Figure 17:
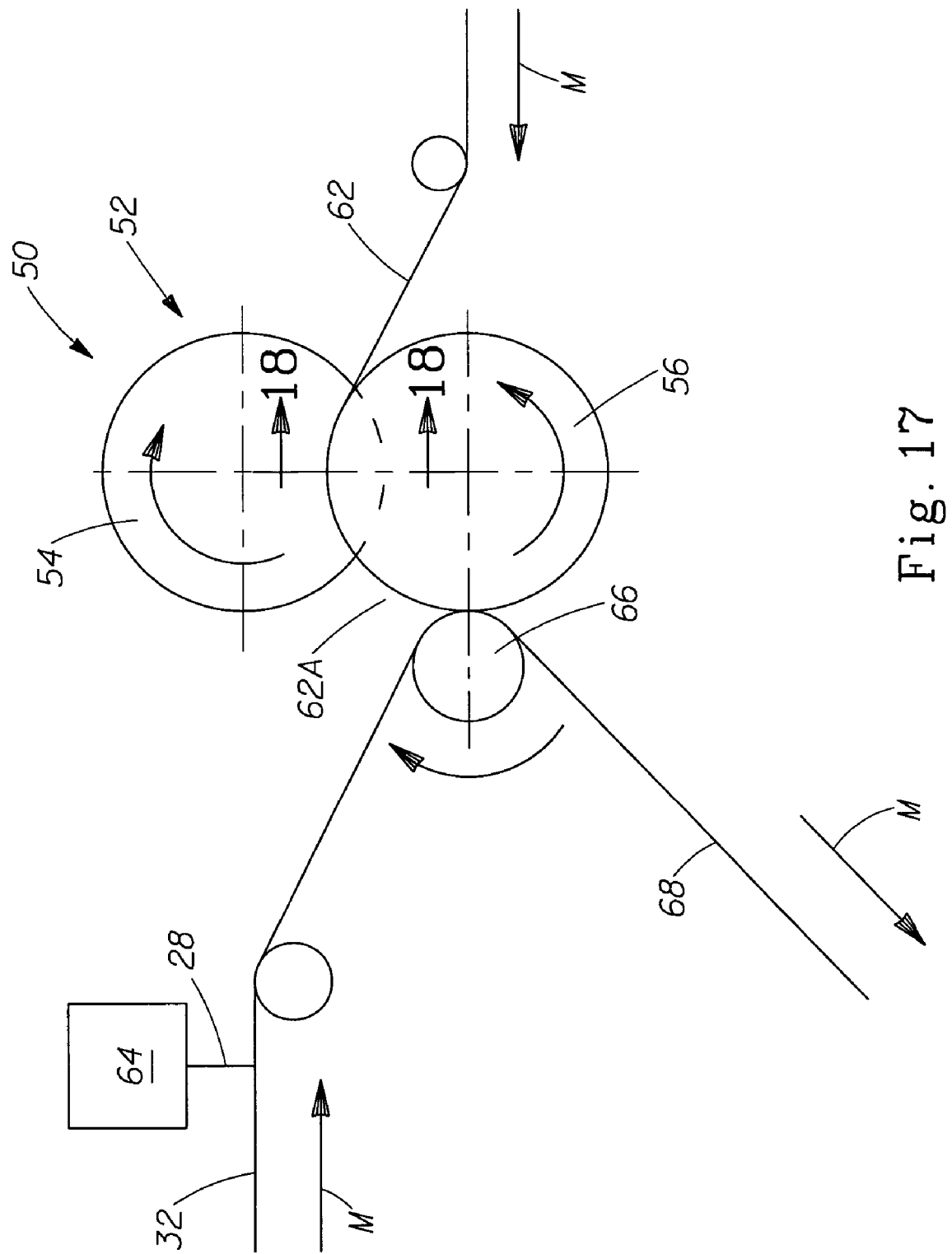
FIG. 17 is a simplified process diagram of one embodiment of a method of present invention for manufacturing a corrugated material for the disposable absorbent article of the present invention.
Figure 18:
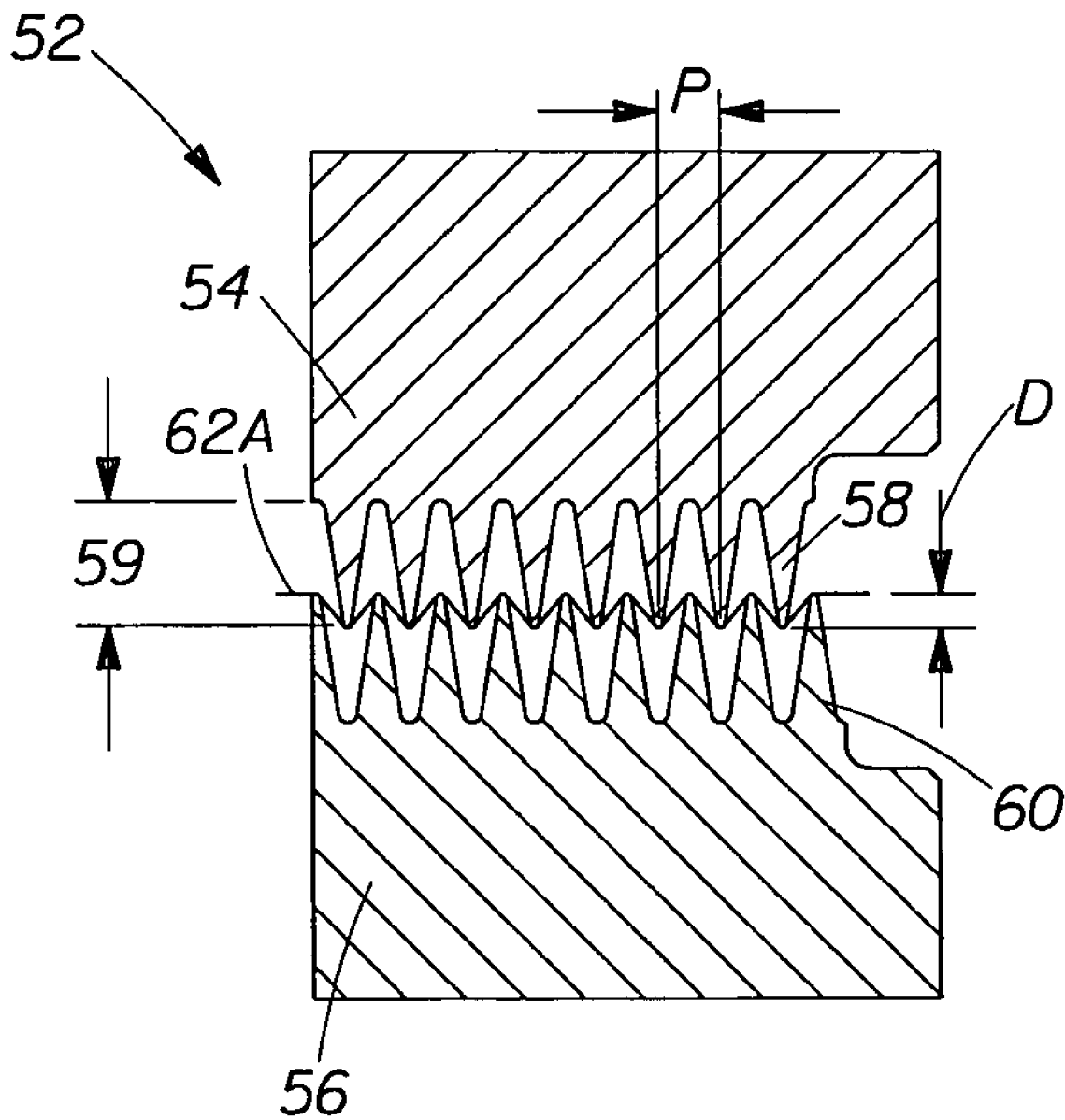
FIG. 18 is a fragmented, enlarged cross-sectional view of ring rolls of the method of FIG. 17 taken along line 18-18.

FIG. 17 is a simplified process diagram 50 of a method of the present invention for manufacturing a corrugated material for the wings or both the wings and the backsheet of the disposable absorbent articles of the present invention described above. The diagram 50 shows a ring-rolling device 52 including at least a pair of corrugated or ring rolls 54 and 56. The ring rolls 54 and 56 have a multiplicity of teeth forming ridges and recesses therebetween on the outer surfaces of the rolls 54 and 56. As noted above, the ridges and recesses of the ring rolls 54 and 56 can extend in any suitable direction; however, FIG. 17 illustrates an embodiment where the ridges and recesses extend parallel to the machine direction or the longitudinal direction of the process.

FIG. 18 is a fragmented, exploded cross-sectional view of the ring rolls 54 and 56 of FIG. 6 taken along line 18-18, wherein the teeth 58 of the ring roll 54 and the teeth 60 of the ring roll 56 are engaged at a depth D, measured between the crests of the engaged teeth 58 and 60. The teeth 58 and 60 have a pitch P and a height 59, both of which can vary within desired ranges, as noted above.

Referring again to FIG. 17, showing a material 62, which can be provided to the corrugated or ring rolls 54 and 56 in any conventional manner from a material roll (not shown) for passing between the engaged, counter-rotating ring rolls 54 and 56 in order to be deformed by the corrugations, i.e., the engaged teeth 58 and 60, into a corrugated material having a multiplicity of corrugations comprising ridges 26 and groves 24 (as shown in FIG. 10) having the pitch P and the height H, and extending in the direction of the movement of the material 62, which is a web or machine direction M.

The ring rolls 54 and 56 of the present invention are preferably heated to provide a desired heat treatment step to the material 62 during the ring-rolling step. The heat treatment step of the method of the present invention is important for providing a material memory to the corrugated material and, thus, greater stability to maintaining the pitch P and height H of the ridges 26 and groves 24 of the corrugated material, formed by the ring roll step.

The above heat treatment can be provided by any suitable means including use of suitable heat cartridges installed in the ring rolls 54 and 56 or by any other suitable heat treatment means disposed inside or outside of the ring rolls 54 and 56. For example, the inside means can include heat cartages disposed inside the ring rolls 54 and 56 (or at least one ring roll, preferably, the ring roll around which the material 62 at least partially wraps); and the outside means can include a hot air blow, and the like.

The heat treatment temperature can be any suitable temperature, depending on the material 62 and the velocity at which the material 62 is ring rolled, i.e., the time of the heat treatment. In generally, the heat treatment temperature should be less than the melting point of the material(s) comprising the material 62.

After passing between the teeth 58 and 60 of the ring rolls 54 and 56, respectfully, the material 62 becomes a corrugated material 62A and remains on the surface of one of the ring rolls, for example, the ring roll 56, until the corrugated material 62A is combined with the glue strips 28 (FIG. 17) and the release material 32.

The release material 32 can be provided to the ring roll 56 in any conventional manner from a material roll (not shown). Before combining with the corrugated material 62A at the ring roll 56, the release material 32 is provided with a multiplicity of glue strips 28 directed in the machine direction M. The glue strips 28 are separated from each other in the cross-machine direction at a pitch P, which is the same pitch P that is between the adjacent teeth or ridges of the ring rolls 54 and 56. The glue strips 28 can be provided to the release material 32 by any suitable conventional means, for example, as shown in FIG. 17, by a glue applicator 64, which can include a conventional slot applicator, available, for example, from Nordson Corp. The glue strips 28 can be of any suitable width (in the cross-machine direction), for example, 1 mm wide. The glue strips 28 can be preferably provided at a suitable proximity to the ring roll 56, in order to provide desired alignment of the glue strips 28 with the corrugations of the ring roll 56. This alignment is needed in order to apply the glue strips 28 to the crests 30 of the ridges 26 of the corrugated material 62A, as shown in FIG. 10. This alignment of the release material 32 in the cross-machine direction with the corrugations of the ring roll 56 can be provided by any suitable means known in the art of handling continuous webs in production of disposable absorbent articles.

FIG. 17 further shows a nip roll 66 for providing a sufficient pressure for attaching the glue strips 28 to the crests 30 of the ridges 26 of the corrugated material 62A. The nip roll 66 can be any suitable nip roll known in the art of production of disposable absorbent articles.

After the nip roll 66, the corrugated material 62A and the release material 32 with glue strips 28 therebetween form together a composite material 68, which then can be used in the production of disposable feminine hygiene article of the present invention.

Figure 19:
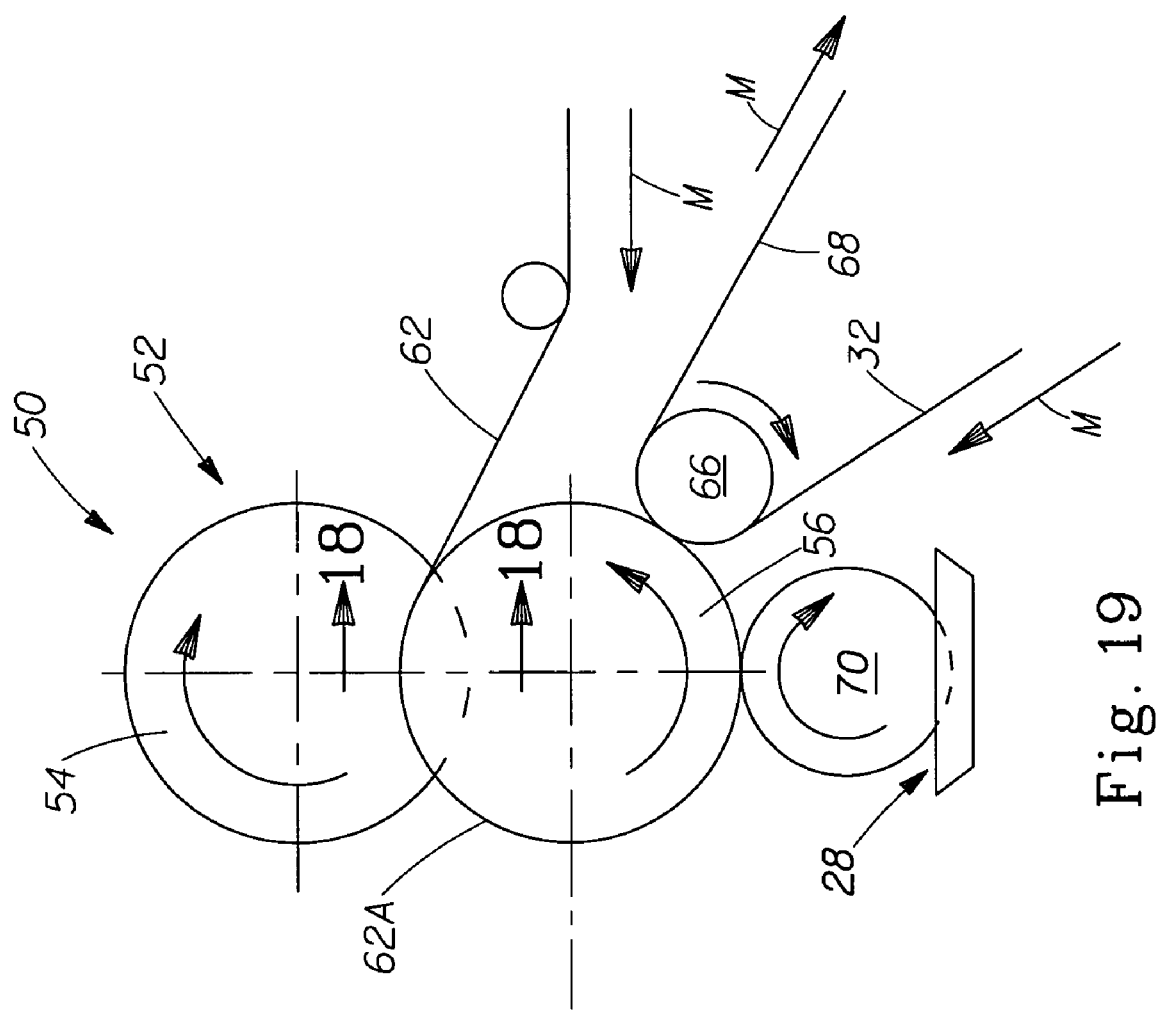
FIG. 19 is a simplified process diagram of another embodiment of the method of present invention for manufacturing the corrugated material for the disposable absorbent article of the present invention.

Alternatively, as shown in FIG. 19, the glue 28 can be provided directly to the crests 30 of the ridges 26 of the corrugated material 62A by a conventional "kissing" technology or glue-printing technology (for example, Guttenberg printing method known to one skilled in the art), which can utilize as a glue applicator a roll having a smooth or micro embossed outer surface coated by a thin layer of glue that comes in contact with protrusions on a printing surface (a 3D surface, which can have protrusions of any suitable size and shape, oriented in any direction in relation to the machine direction). As shown in FIG. 19, which is a simplified process diagram 50A of the alternative method of the present invention for manufacturing a corrugated material for the wings or both the wings and the backsheet of the disposable absorbent articles of the present invention described above, a glue-covered roll 70 having a thin layer of glue 28 can comes in contact with the crests 30 of the ridges 26 of the corrugated material 62A to transfer the glue from the glue-covered roll 70 to the crests 30 prior to combining the corrugated material 62A with the release material 32.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having one or more side flaps or wings, comprising:
   (a) a fluid-pervious topsheet a fluid-impervious backsheet opposing said topsheet, and an absorbent core disposed between said topsheet and said backsheet, said article having a longitudinal direction and a transverse direction perpendicular thereof;
   (b) said one or more wings extending in said transverse direction and comprising at least one corrugated region including a multiplicity of ridges and recesses, said ridges rising toward a garment-facing surface of said article and having glue strips attached to crests of said ridges; and
   (c) a release material for covering said at least one corrugated region, said release material contacting said glue strips.

2. The article of claim 1, wherein said article is a catamenial napkin for absorbing menses or an incontinence pad for absorbing urine.

3. The article of claim 1, wherein said multiplicity of ridges and recesses extend in a direction perpendicular to said longitudinal direction.

4. The disposable absorbent article of claim 1, wherein said multiplicity of ridges and recesses extend in a direction parallel to said longitudinal direction.

5. The disposable absorbent article of claim 1, wherein said multiplicity of ridges and recesses extend in a direction forming an angle with said longitudinal direction, said angle being greater than 0 degrees and less than 90 degrees.

6. The disposable absorbent article of claim 1, wherein said at least one corrugated region includes a multiplicity of said ridges and recesses extending in a direction that is different from a multiplicity of ridges and recesses of a second corrugated region.

7. The article of claim 1, wherein said ridges and recesses have a pitch ranging from about 1 mm to about 5 mm.

8. The article of claim 1, wherein said ridges and recesses have a height ranging from about 1 mm to about 6 mm.

9. The article of claim 1, wherein said backsheet comprises at least one corrugated region.

10. A method of producing a composite material including a corrugated material, a release material opposed thereto, and a multiplicity of glue ships disposed between the release material and the corrugated material and attached to the crests of the corrugated material, the method comprising the steps of:
    (a) providing at least two corrugating rolls, counter-rotating and engaged with each other, said corrugating rolls having a multiplicity of ridges and recesses disposed on the outer surfaces of said corrugating rolls, said ridges extending perpendicularly to axes of rotation of said corrugating roll and being separated from each other at a pitch;
    (b) providing a first material between said corrugating rolls for deforming said first material into a corrugated material having a multiplicity of ridges and recesses;
    (c) heat-treating said corrugated material at a temperature less than the melting temperature of said first material;
    (d) providing a release material having a multiplicity of glue strips disposed in a machine direction and at said pitch therebetween; and
    (e) combining said release material with said corrugated material, wherein said multiplicity of glue strips are attached to crests of said ridges of said corrugated material to form said composite material.

11. The method of claim 10, wherein said pitch between said groves of said ring rolls is from about 1 mm to about 5 mm.

12. The method of claim 10, wherein the step of providing a release material further comprises the step of depositing a multiplicity of glue strips by a glue applicator.

13. The method of claim 10, wherein said glue applicator is a slot applicator.

14. The method of claim 10, wherein the step of combining further comprises the step of pressing said release material against said corrugated material to attach said glue strips to said ridges of said corrugated material.

15. The method of claim 10, wherein said composite material comprises a wing of a disposable absorbent article.

16. The method of claim 10, wherein said composite material comprises a backsheet of a disposable absorbent article.

17. A method of producing a composite material including a corrugated material, a release material opposed thereto, and a multiplicity of glue strips disposed between the release material and the corrugated material and attached to the crests of the corrugated material, the method comprising the steps of:

(a) providing at least two corrugating rolls, counter-rotating and engaged with each other, said corrugating rolls having a multiplicity of ridges and recesses disposed on the outer surfaces of said corrugating rolls, said ridges extending perpendicularly to axes of rotation of said corrugating roll and being separated from each other at a pitch;

(b) providing a first material between said corrugating rolls for deforming said first material into a corrugated material having a multiplicity of ridges and recesses;

(c) heat-treating said corrugated material at a temperature less than the melting temperature of said first material;

(d) providing a glue-covered roll for contacting crests of said ridges of said corrugated material with a glue to transfer said glue from said glue-covered roll to said crests of said ridges of said corrugated material;

(e) providing a release material; and (f) combining said release material with said corrugated material, wherein said glue at said crests is disposed between said corrugated material and said release material to form said composite material.

18. The method of claim 17, wherein said pitch between said groves of said ring rolls is from about 1 mm to about 5 mm.

19. The method of claim 17, wherein said composite material comprises a wing of a disposable absorbent article.

20. The method of claim 17, wherein said composite material comprises a backsheet of a disposable absorbent article.

* * * * *